(12) United States Patent
Park et al.

(10) Patent No.: US 8,647,823 B2
(45) Date of Patent: Feb. 11, 2014

(54) POLYNUCLEOTIDE SYNTHESIS ON A MODIFIED SURFACE

(75) Inventors: Joon-Won Park, Pohang (KR);
Bong-Jin Hong, Pohang (KR)

(73) Assignees: Postech Foundation, Pohang (KR);
Posco, Pohang (KR)

( * ) Notice: Subject to any disclaimer, the term of this patent is extended or adjusted under 35 U.S.C. 154(b) by 798 days.

(21) Appl. No.: 11/625,793

(22) Filed: Jan. 22, 2007

(65) Prior Publication Data

US 2008/0064070 A1 Mar. 13, 2008

Related U.S. Application Data

(63) Continuation-in-part of application No. 11/459,626, filed on Jul. 24, 2006, now abandoned.

(60) Provisional application No. 60/701,848, filed on Jul. 22, 2005.

(51) Int. Cl.
*C12Q 1/68* (2006.01)
*C12P 19/34* (2006.01)
*C07H 21/04* (2006.01)
*C07H 21/00* (2006.01)

(52) U.S. Cl.
USPC ......... 435/6.12; 435/6.1; 435/91.1; 435/91.2; 536/24.33; 536/25.3

(58) Field of Classification Search
USPC ............. 435/6.1, 6.12, 91.1, 91.2; 536/24.33, 536/25.3
See application file for complete search history.

(56) References Cited

U.S. PATENT DOCUMENTS

| | | | |
|---|---|---|---|
| 5,667,976 A * | 9/1997 | Van Ness et al. ................. | 435/6 |
| 6,051,377 A * | 4/2000 | Mandecki ......................... | 435/6 |
| 6,376,191 B1 * | 4/2002 | Yu et al. ........................... | 435/6 |
| 6,451,260 B1 * | 9/2002 | Dusterhoft et al. .......... | 422/68.1 |
| 6,692,917 B2 | 2/2004 | Neri | |
| 2003/0199577 A1 * | 10/2003 | Park et al. ..................... | 514/489 |
| 2004/0009500 A1 * | 1/2004 | Benters et al. .................... | 435/6 |
| 2005/0037413 A1 * | 2/2005 | Park et al. ......................... | 435/6 |
| 2005/0059068 A1 | 3/2005 | Huang | |

FOREIGN PATENT DOCUMENTS

WO   WO 02/33412   4/2002

OTHER PUBLICATIONS

Shchepinov et al, Oligonucleotide dendrimers: Synthesis and use as polylabelled DNA probes., 1997, Nucleic Acids Research, 25, 4447-4454.*
Hong et al, Nanosclae controlled spacing provides DNA microarrays with the SNP discrimination efficiency in solution phase, 2005, Langmuir, 21, 4257-4261.*
Hong et al Supporting document, Langmuir, 2005, 21, 4257-4261.*
Mitterer et al, Microarray based identification of bacteria in clinical samples by solid phase PCR amplification of 23S ribosomal DNA sequences, 2004, Journal of clinical microbiology, 42, 1048-1057.*
Benters-2 et al, DNA microarrays with PAMAM dendritic linker systems, 2002, Nucleic Acids Research, 30, e10, pp. 1-7.*
Choi et al, Efficient protein—ligand interaction by guaranteeing mesospacing between immobilized biotins, 2004, Chem. Commun., 11, 1316-1317.*
Choi et al, Supplemental information, Efficient protein—ligand interaction by guaranteeing mesospacing between immobilized biotins, 2004, Chem. Commun., 11, pp. 1-7.*
Kim et al, Effects of lateral spacing on enzymatic on-chip DNA polymerization, 2011, Biosensors and Bioelectronics, 26, 2566-2573.*
Dodge et al. "A microfluidic platform using molecular beacon-based temperature calibration for thermal dehybridization of surface-bound DNA", Anal. Chem. 2004, 76, 1778-1787.

* cited by examiner

*Primary Examiner* — Narayan Bhat
(74) *Attorney, Agent, or Firm* — Don D. Cha; Hamilton DeSanctis & Cha, LLP

(57) ABSTRACT

The present invention relates to a method for the synthesis of a polynucleotide on a modified surface of a substrate, wherein the modified surface is obtained by chemically modifying with macromolecules in which a plurality of termini of the branched region are bound to the surface and a terminus of the linear region is functionalized.

18 Claims, 10 Drawing Sheets

SEQUENCE LISTING

```
<160> NUMBER OF SEQ ID NOS: 14

<210> SEQ ID NO 1
<211> LENGTH: 10
<212> TYPE: DNA
<213> ORGANISM: Artificial Sequence
<220> FEATURE:
<223> OTHER INFORMATION: DNA used in Example 2

<400> SEQUENCE: 1
tttttttttt                                                         10

<210> SEQ ID NO 2
<211> LENGTH: 15
```

```
<212> TYPE: DNA
<213> ORGANISM: Artificial Sequence
<220> FEATURE:
<223> OTHER INFORMATION: DNA used in Example 3

<400> SEQUENCE: 2
acaagcacag ttagg                                                    15

<210> SEQ ID NO 3
<211> LENGTH: 19
<212> TYPE: DNA
<213> ORGANISM: Artificial Sequence
<220> FEATURE:
<223> OTHER INFORMATION: Primer 1

<400> SEQUENCE: 3
gatcaccagc ggcatcgag                                                19

<210> SEQ ID NO 4
<211> LENGTH: 19
<212> TYPE: DNA
<213> ORGANISM: Artificial Sequence
<220> FEATURE:
<223> OTHER INFORMATION: Primer 2

<400> SEQUENCE: 4
gatcaccacc ggcatcgag                                                19

<210> SEQ ID NO 5
<211> LENGTH: 20
<212> TYPE: DNA
<213> ORGANISM: Artificial Sequence
<220> FEATURE:
<223> OTHER INFORMATION: Primer 3

<400> SEQUENCE: 5
cgatcaccaa cggcatcgag                                               20

<210> SEQ ID NO 6
<211> LENGTH: 20
<212> TYPE: DNA
<213> ORGANISM: Artificial Sequence
<220> FEATURE:
<223> OTHER INFORMATION: Primer 4

<400> SEQUENCE: 6
cgatcaccat cggcatcgag                                               20

<210> SEQ ID NO 7
<211> LENGTH: 17
<212> TYPE: DNA
<213> ORGANISM: Artificial Sequence
<220> FEATURE:
<223> OTHER INFORMATION: Primer 5

<400> SEQUENCE: 7
atcacccgcg gcatcga                                                  17

<210> SEQ ID NO 8
<211> LENGTH: 22
<212> TYPE: DNA
<213> ORGANISM: Artificial Sequence
<220> FEATURE:
<223> OTHER INFORMATION: Primer 6 used in Example 5

<400> SEQUENCE: 8
ctggaagagc tcgtatggca cc                                            22
```

```
<210> SEQ ID NO 9
<211> LENGTH: 21
<212> TYPE: DNA
<213> ORGANISM: Artificial Sequence
<220> FEATURE:
<223> OTHER INFORMATION: Primer 7 used in Example 5

<400> SEQUENCE: 9
gccgtacagg atctcgagga a                                              21

<210> SEQ ID NO 10
<211> LENGTH: 19
<212> TYPE: DNA
<213> ORGANISM: Artificial Sequence
<220> FEATURE:
<223> OTHER INFORMATION: Ligand 1 used in Example 6

<400> SEQUENCE: 10
gatcaccagc ggcatcgag                                                 19

<210> SEQ ID NO 11
<211> LENGTH: 19
<212> TYPE: DNA
<213> ORGANISM: Artificial Sequence
<220> FEATURE:
<223> OTHER INFORMATION: Ligand 2 used in Example 6

<400> SEQUENCE: 11
gatcaccacc ggcatcgag                                                 19

<210> SEQ ID NO 12
<211> LENGTH: 20
<212> TYPE: DNA
<213> ORGANISM: Artificial Sequence
<220> FEATURE:
<223> OTHER INFORMATION: Ligand 3 used in Example 6

<400> SEQUENCE: 12
cgatcaccaa cggcatcgag                                                20

<210> SEQ ID NO 13
<211> LENGTH: 20
<212> TYPE: DNA
<213> ORGANISM: Artificial Sequence
<220> FEATURE:
<223> OTHER INFORMATION: Ligand 4 used in Example 6

<400> SEQUENCE: 13
cgatcaccat cggcatcgag                                                20

<210> SEQ ID NO 14
<211> LENGTH: 17
<212> TYPE: DNA
<213> ORGANISM: Artificial Sequence
<220> FEATURE:
<223> OTHER INFORMATION: Ligand 5 used in Example 6

<400> SEQUENCE: 14
atcacccgcg gcatcga                                                   17
```

POLYNUCLEOTIDE SYNTHESIS ON A MODIFIED SURFACE

CROSS REFERENCE TO RELATED APPLICATION

The present application is a continuation-in-part of U.S. application Ser. No. 11/459,626, filed on Jul. 24, 2006, still pending, which claims priority to U.S. Provisional Patent Application No. 60/701,848, filed on Jul. 22, 2005, the contents of which are incorporated by reference herein in their entirety.

FIELD OF THE INVENTION

The present invention relates to a method for synthesis of a polynucleotide on modified surface of substrate, where the modified substrate is obtained by chemically modifying with the hyper-branched macromolecules in which a plurality of termini of the branched region of the macromolecules are bound to the surface and a terminus of the linear region of the macromolecules is functionalized.

BACKGROUND OF THE INVENTION

The Polymerase Chain Reaction (PCR) technology has played an important role in biotechnology, and no technique which could replace the PCR technology has yet been developed. Accordingly, the PCR technology will continue to have an essential position in the field of biotechnology in the future.

In addition to the development of the PCR technique, the Reverse Transcriptase-Polymerase Chain Reaction (RT-PCR) technique which is a method of analyzing the gene expression based on the PCR technique was invented. The RT-PCR has a higher sensitivity in detection of a small amount of RNA molecule than a Northern blot analysis, a dot blot analysis, and a nuclease protection method, and is simpler than in situ hybridization. In particular, the RT-PCR is very useful in analyzing various samples in very small amounts, and therefore, the RT-PCR method is also widely used in clinical diagnosis.

Based on these advantages of the PCR and RT-PCR methods, many attempts have been made to combine the methods with high throughput and highly parallel method such as microarray. However, unlike the PCR or RT-PCR which is typically performed in a solution, the reactions which happen on a solid surface has many disadvantages to be overcome such as non-specific adsorption, steric hindrance and electrostatic interaction between biomolecules, etc. Specifically, when a high temperature condition is required like PCR or RT-PCR, the organic thin film coated on the surface has to show high thermal stability.

A Glass or gold substrate have generally been used as a solid support for immobilizing a biomolecule in a biosensor or a microarray, and they are coated with an organic layer which holds the biomolecule. However, because most of silane or thiol compounds forming the organic layer are attached onto these solid supports via Si—O or Au—S bond which is unstable in a buffer solution at a high temperature, it is difficult to hold the biomolecules on the substrate surface. Therefore, first of all, the thermal stability of the organic layer on the surface should be secured to perform PCR or RT-PCR on the surface using these solid supports.

SUMMARY OF THE INVENTION

In the present invention, the present inventors enhanced remarkably the thermal stability of the organic layer and the biomolecule tethered on that layer by introducing a dendron and a specific silane compound onto the substrate surface. Also, the enhanced thermal stability of the dendron-modified surface could allow a polynucleotide to be synthesized on surface at a variable temperature range. Because this result can allow simultaneously performing a PCR process and a detection process of PCR products using a DNA sensor or a DNA microarray, we can not only save time and cost of both PCR and detection processes, but also improve the detection sensitivity by minimizing the loss of target products resulting from the previous method that each process run independently and sequentially. Therefore, these outstanding features of the dendron-modified surface can be successfully applied to POCT (point of care technology), lab-on-a-chip, and other related fields.

The object of present invention is to synthesize a polynucleotide synthesis of a polynucleotide on a modified surface of substrate, wherein the modified surface comprises a molecular layer of regularly spaced size-controlled macromolecules which have a branched region of the macromolecules with a plurality of termini bound to the surface and a linear region with a functionalized terminus. More preferably, this invention provides a method of synthesizing a polynucleotide on a dendron-modified surface of a substrate, wherein the dendron-modified surface is obtained by chemically modifying with a dendron in which a plurality of termini of the branched region of the dendron are bound to the surface and a terminus of the linear region of the dendron is functionalized. In particular, the polynucleotide may be DNA, RNA, oligonucleotide, cDNA, nucleotide analog, or a combination thereof.

In the above-described invention, the synthesis of the polynucleotide is carried out by a polymerase. In particular, the polymerase may be DNA polymerase, RNA polymerase, Tag polymerase, or polymerase derived from Taq polymerase, Klenow DNA polymerase I, reverse transcriptase. Further, the synthesis of polynucleotide is carried out by using PCR, real time PCR, RT-PCR (reverse transcription PCR) or random priming method.

In the above-describe invention, the synthesis of polynucleotide may be carried out at a temperature of 25 to 100° C. Further, the synthesis of polynucleotide may be carried out at a temperature of 60 to 95° C. Still further, the synthesis of polynucleotide may be carried out at a temperature of 30 to 40° C.

In the present invention, a target-specific ligand selected from the group consisting of primers, a polymerase, a template DNA, RNA, or a probe is bound to the terminus of the linear region of the macromolecule. A probe binds to the synthesized polynucleotide and is selected from the group consisting of a chemical compound, DNA, RNA, PNA, aptamer, peptide, polypeptide, carbohydrate, antibody, antigen, biomimetics, nucleotide analog, and a combination thereof.

The target-specific ligand is fixed to the terminus of the linear region, comprising the steps of optionally removing protecting group from the terminus of the linear region of the dendrons on the substrate; and contacting the target-specific ligand or a linker molecule connected to the target-specific ligand to the terminus of the linear region so that the ligand or the linker molecule and the terminus form a bond. The linker molecule is a homobifunctional or heterobifunctional linker.

The target-specific ligand is located on the modified surface at a density ranging from about 0.001 ligand/nm2 to about 0.2 ligand/nm2. Still further, the distance between target-specific ligands bound to the linear region of the macromolecule may be from about 0.1 to about 100 nm. In particular, the distance between target-specific ligands bound to the linear region of the macromolecule may be from about 1 to about 10 nm.

In another embodiment of the invention, the polynucleotide is synthesized by reacting (a) at least one primer immobilized on the modified surface, with (b) a solution comprising polymerase, dNTP or NTP, and template DNA or RNA.

In further embodiment of the present invention, the polynucleotide is synthesized by reacting (a) template DNA or RNA immobilized on the modified surface, with (b) a solution comprising polymerase, dNTP or NTP, and primers.

In still further embodiment of the present invention, the polynucleotide is synthesized by reacting (a) polymerase immobilized on the modified surface, with (b) a solution comprising dNTP or NTP, primers, and template DNA or RNA.

In further embodiment of the invention, the polynucleotide is synthesized by reacting dNTP or NTP, primers, template DNA or RNA, and polymerase in a solution covered on the modified surface and is bound to the probe immobilized on the modified surface.

Another present invention is directed to a modified surface of a substrate, wherein the modified surface comprises a molecular layer of regularly spaced size-controlled macromolecules which have branched region of the macromolecules with a plurality of termini bound to the surface and the linear region with a functionalized terminus. More preferably, the present invention relates to a dendron-modified surface is obtained by chemically modifying with a dendron in which a plurality of termini of the branched region are bound to the surface and a terminus of the linear region of the dendron is functionalized. On the surface, the macromolecules may be spaced at regular intervals between about 0.1 nm and about 100 nm among the linear functionalized groups. In particular, the macromolecules may be spaced at regular intervals between about 1 nm and about 10 nm among the linear functionalized groups.

In the above-described surface, the terminus of the branched region is functionalized with —COZ, —NHR, —OR', or —PR"$_3$, wherein Z is a leaving group, R is an alkyl, R' is alkyl, aryl, or ether, and R" is H, alkyl, or alkoxy. In particular, COZ may be acid, ester, activated ester, acid halide, activated amide, or CO-imidazoyl; R may be $C_1$-$C_4$ alkyl, and R' may be $C_1$-$C_4$ alkyl.

Further, wherein the linear region comprises a spacer region which comprises a linker region covalently bound to the first functional group and is connected to the branched region via a first functional group. The first functional group may be without limitation —NH_, —O—, —PH$_2$—, —COO—, —CO— or —S—. Still further, the spacer region may comprise a linker region covalently bound to the first functional group.

In the surface described above, the linker region may comprise a substituted or unsubstituted alkyl, alkenyl, alkynyl, cycloalkyl, aryl, ether, polyether, ester, or aminoalkyl group. Still further, the spacer region may further comprise a second functional group which is connected to the linker region and is located at the terminus of the linear region. The second functional group may include without limitation —NH_, —O—, —PH$_2$—, —COO—, —CO— or —S—. A protecting group may be bound to the terminus of the linear region. Such protecting group may be acid labile or base labile.

In yet another embodiment of the invention, the substrate described above may be made of semiconductor, synthetic organic metal, synthetic semiconductor, metal, alloy, plastic, silicon, silicate, glass, or ceramic. In particular, the substrate may be without limitation a slide, particle, bead, micro-well, or porous material. The porous material may be a membrane, gelatin or hydrogel. And further in particular, the bead may be a controlled pore bead.

The method according to the present invention, the modified surface of a substrate is manufactured by functionalizing and contacting the substrate to react with a plurality of termini of the branched region of the dendron so that the termini and the substrate form a bond covalently or ionically.

These and other objects of the invention will be more fully understood form the following description of the invention, the referenced drawings attached hereto and the claims appended hereto.

BRIEF DESCRIPTION OF THE DRAWING

A more complete appreciation of the invention, and many of the attendant advantages thereof, will be readily apparent as the same becomes better understood by reference to the following detailed description when considered in conjunction with the accompanying drawing, wherein.

DETAILED DESCRIPTION

Figure 1A:
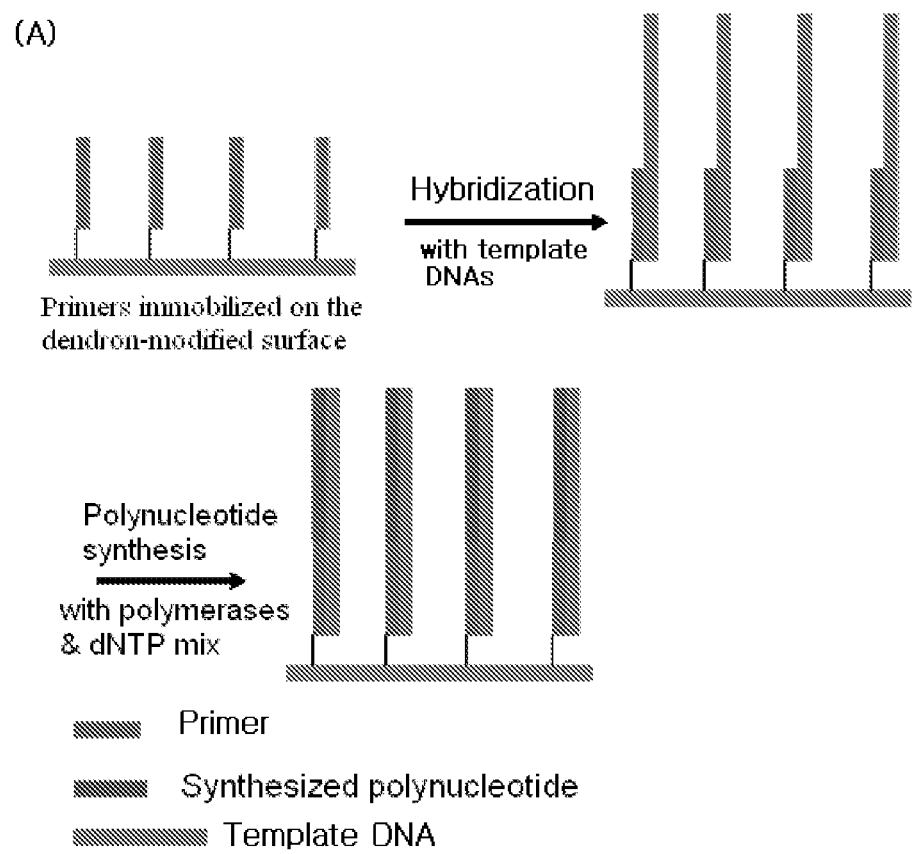
FIG. 1 is a schematic view showing "polynucleotide synthesis" on the dendron-modified surface: (A) The polynucleotide synthesis is performed by reacting the primers immobilized on the dendron-modified surface with free template DNA under the presence of free enzyme; (B) the polynucleotide synthesis is performed by reacting template DNA immobilized on the dendron-modified surface with the free primers under the presence of free enzyme; (C) the polynucleotide synthesis is performed by reacting the free DNA template with the free primers under the presence of enzyme immobilized on the dendron-modified surface; (D) the polynucleotide synthesis is performed by reacting the free DNA template, the free primers, and the free enzyme in solution covered on the dendron-modified surface and simultaneously the synthesized polynucleotide is bound with the target-specific ligand immobilized on the surface.
Figure 1B:
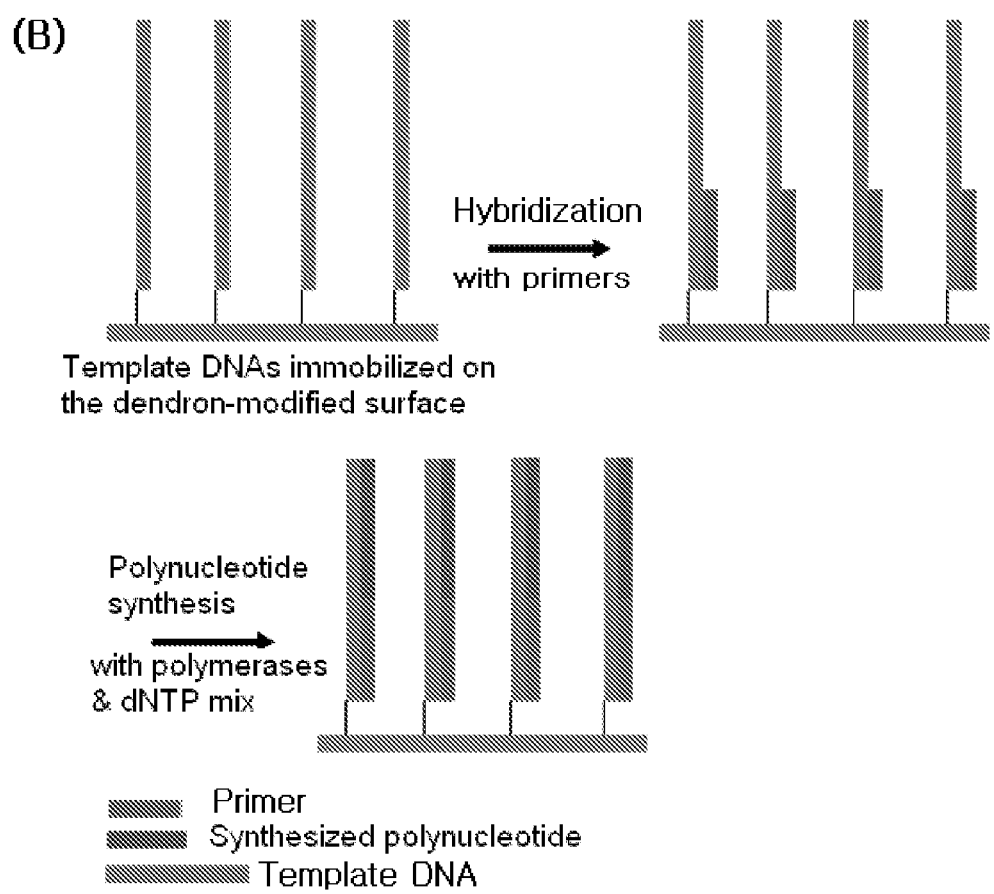
Figure 1C:
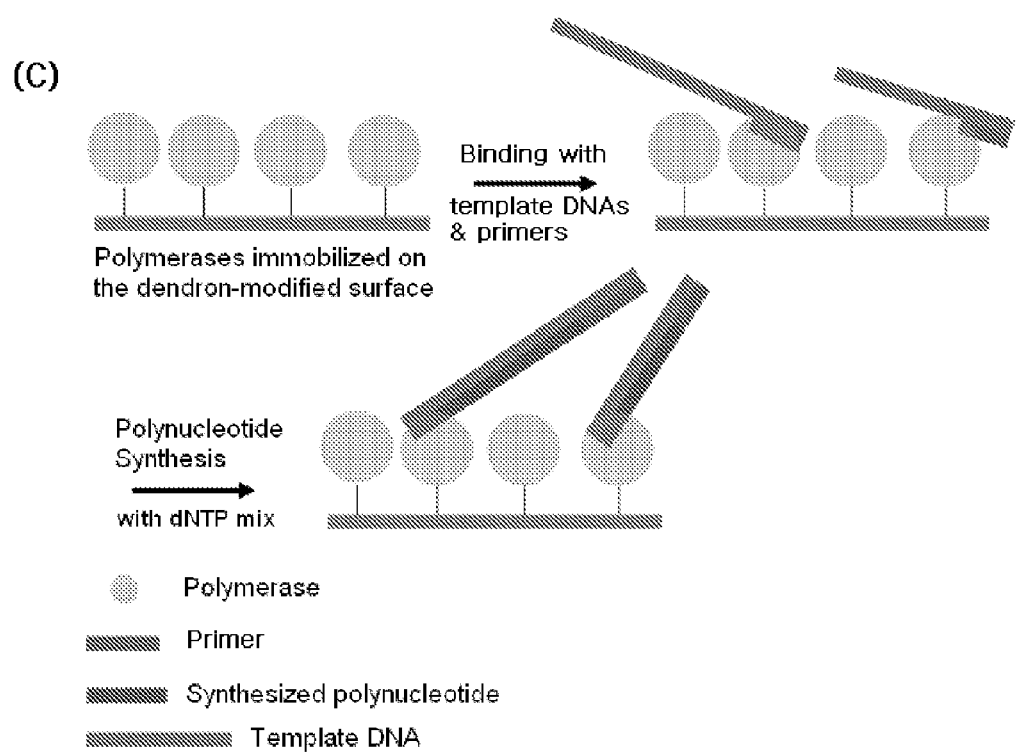
Figure 1D:
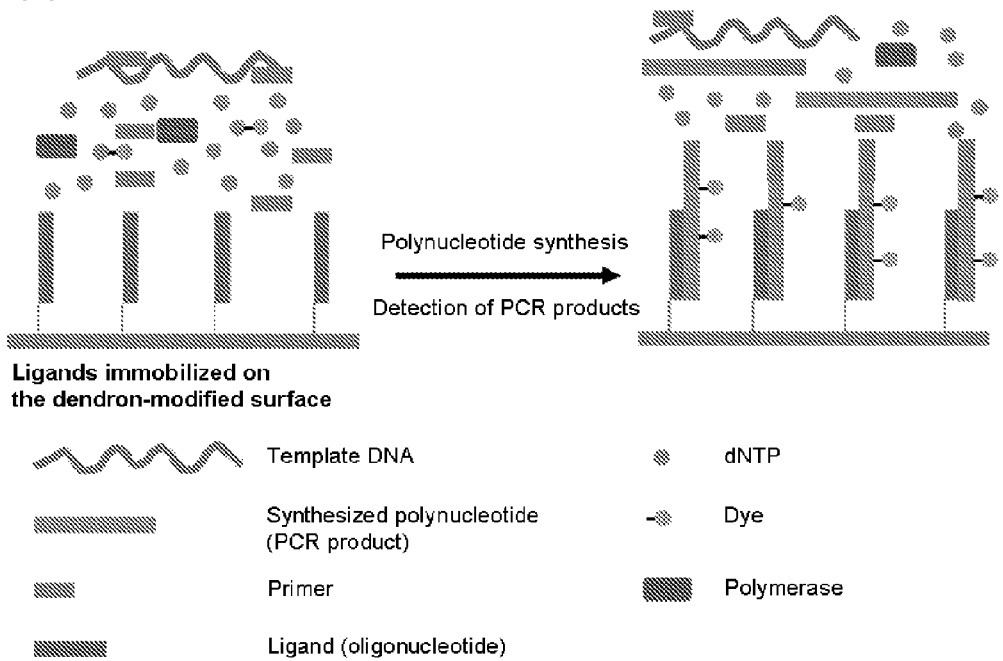
Figure 2:
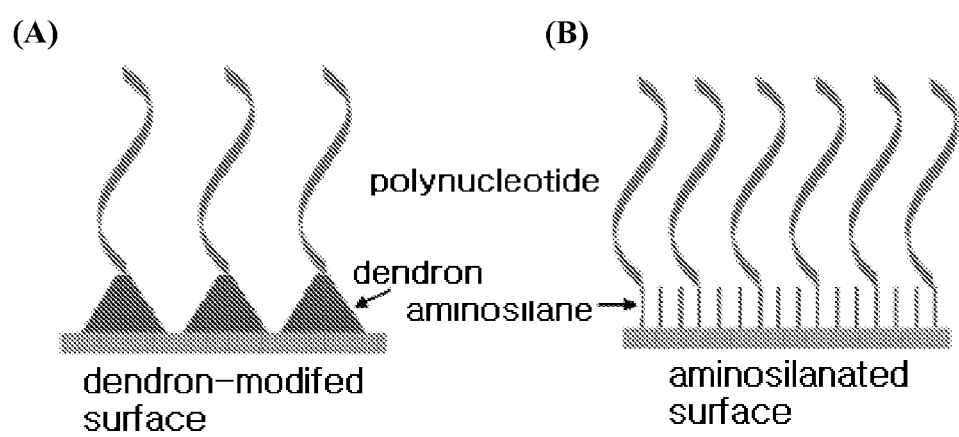
FIG. 2 is a schematic view showing DNA immobilized on the surface, (A) the dendron-modified surface of a solid support, and (B) a generic surface of a solid support such as aminosilanated surface.

In the present application, "a" and "an" are used to refer to both single and a plurality of objects.

As used herein, "aptamer" means a single-stranded, partially single-stranded, partially double-stranded or double-stranded nucleotide sequence, advantageously replicatable nucleotide sequence, capable of specifically recognizing a selected nonoligonucleotide molecule or group of molecules by a mechanism other than Watson-Crick base pairing or triplex formation.

As used herein, "bifunctional," "trifunctional" and "multifunctional," when used in reference to a synthetic polymer or multivalent homo- or heteropolymeric hybrid structure, mean bivalent, trivalent or multivalent, as the case may be, or comprising two, three or multiple specific recognition elements, defined sequence segments or attachment sites.

As used herein, "biomimetic" means a molecule, group, multimolecular structure or method that mimics a biological molecule, group of molecules, structure.

As used herein, "dendritic molecule" is a molecule exhibiting regular dendritic branching, formed by the sequential or generational addition of branched layers to or from a core.

As used herein, "dendritic polymer" is a polymer exhibiting regular dendritic branching, formed by the sequential or generational addition of branched layers to or from a core. The term dendritic polymer encompasses "dendrimers", which are characterized by a core, at least one interior branched layer, and a surface branched layer (see, e.g., Petar et al. Pages 641-645 In Chem. in Britain, (August 1994).

A "dendron" is a species of dendrimer having branches emanating from a focal point, which is or can be joined to a core, either directly or through a linking moiety to form a dendrimer. Many dendrimers include two or more dendrons joined to a common core. However, the term "dendrimer" may be used broadly to encompass a single dendron.

As used herein, "branched" as it is used to describe a macromolecule or a dendron structure is meant to refer to a plurality of polymers having a plurality of termini which are able to bind covalently or ionically to a substrate. In one embodiment, the macromolecule containing the branched or hyperbranched structure is "pre-made" and is then attached to a substrate.

As used herein, "immobilized" means insolubilized or comprising, attached to or operatively associated with an insoluble, partially insoluble, colloidal, particulate, dispersed, suspended and/or dehydrated substance or a molecule or solid phase comprising or attached to a solid support.

As used herein, "linker molecule" and "linker" when used in reference to a molecule that joins the branched portion of a size-controlled macromolecule such as a branched/linear polymer to a protecting group or a ligand. Linkers may include, for instance and without limitation, spacer molecules, for instance selected molecules capable of attaching a ligand to a dendron.

As used herein, "low density" refers to about 0.01 to about 0.5 probe/nm2, preferably about 0.05 to about 0.2, more preferably about 0.075 to about 0.15, and most preferably about 0.1 probe/nm2.

As used herein, "regular intervals" refers to the spacing between the tips of the size-controlled macromolecules, which is a distance from about 1 nm to about 100 nm so as to allow room for interaction between the target-specific ligand and the target substantially without steric hindrance. Thus, the layer of macromolecules on a substrate is not too dense for specific molecular interactions to occur.

Herein, the term "polynucleotide synthesis" or "the synthesis of a polynucleotide" includes polynucleotide synthesis, chain extension, and amplification. For example, the term includes DNA or RNA polymerization such as DNA or RNA synthesis, DNA or RNA chain extension, PCR, RT-PCR, random priming, reverse transcription, or the other similar polynucleotide synthesis, chain extension, or any amplification method. The term, "polynucleotide" means DNA, RNA, oligonucleotide, cDNA, nucleotide analog or a combination thereof.

The polynucleotide synthesis on the modified surface is carried out by a polymerase. The polymerase is DNA polymerase including DNA polymerase I, II, and III, modified DNA polymerase, RNA polymerase including RNA polymerase I, II, and III, modified RNA polymerase, Tag polymerase, polymerase derived from Taq polymerase, T7 DNA polymerase, Klenow DNA polymerase, polymerase derived from Klenow DNA polymerase, reverse transcriptase, or modified reverse transcriptase.

The synthesis of the polynucleotide on the dendron-modified surface is carried out at a temperature of 25 to 100° C., preferably 60 to 95° C. or 30 to 40° C. In general, a Tag polymerase or polymerase derived from Taq polymerase which is used for PCR, real time PCR, or RT-PCR synthesizes a polynucleotide under thermal cycle comprising a denaturing step at 90-95° C., an annealing step at 55-70° C., and an extension step at 65-80° C. On the other hand, a Klenow DNA polymerase generally synthesizes a polynucleotide at 35-40° C. without thermal cycle.

A PCR, real time PCR, RT-PCR or random priming method can copy or amplify whole or some part of oligonucleotides, polynucleotides, cDNA, DNAs or RNAs, and a reverse-transcription method like RT-PCR can covert mRNA to cDNA followed by amplifying whole or some part of the cDNA. These all methods include the process of a polynucleotide synthesis in solution phase. Recently, it is being tried to apply these methods onto a surface for manufacturing a PCR chip, biochip, biosensor, POC device, or lab-on-a-chip incorporating the function of the polynucleotide synthesis.

The polynucleotide synthesis on the modified surface can be performed using the following four methods for example.

(i) The polynucleotide is synthesized on the modified surface by reacting (a) at least a primer immobilized on the dendron; with (b) a solution comprising polymerase, dNTP or NTP, and template DNA or RNA.

(ii) The polynucleotide is synthesized on the modified surface by reacting (a) template DNA or RNA immobilized on the dendron; with (b) a solution comprising polymerase, dNTP or NTP, and primers.

(iii) The polynucleotide is synthesized on the modified surface by reacting (a) polymerase immobilized on the dendron; with (b) a solution comprising dNTP or NTP, primers and template DNA or RNA.

(iv) The polynucleotide is synthesized on the modified surface by reacting dNTP or NTP, primers, template DNA or RNA, and polymerase in a solution covered on the dendron-modified surface, and simultaneously the synthesized polynucleotide is bound with a probe which can interact with the synthesized polynucleotide and is immobilized on the dendron-modified surface.

The probe is a chemical compound, polynucleotide, aptamer, peptide, polypeptide, carbohydrate, antibody, antigen, biomimetics, or a combination thereof. In particular, the polynucleotide is DNA, RNA, oligonucleotide, cDNA, PNA, nucleotide analog, or a combination thereof.

The polynucleotide synthesis by a polymerase is carried out on the dendron-modified surface which is covered with a buffer solution. Examples of the buffer solution includes buffer solution 1 (50 mM KCl, 10 mM Tris-HCl, and 1.5 mM $MgCl_2$), buffer solution 2 (10 mM Tris-HCl, 40 mM KCl, 1.5 mM $MgCl_2$), buffer solution 3 (50 mm Tris-HCl, 10 mM $MgCl_2$, 1 mM DTT, 50 μg/ml BSA), and buffer solution 4 (50 mm Tris-HCl, 75 mM KCl, 3 mM $MgCl_2$, and 10 mM DTT) but are not limited thereto.

Unlike the PCR or RT-PCR in solution, the reactions which happen on a solid surface have many disadvantages to be overcome such as non-specific adsorption, steric hindrance, electrostatic interaction between biomolecules, etc. Specifically, when the high temperature condition is required like PCR or RT-PCR, the stability between the surface and organic thin film introduced on the surface must be maintained at a high temperature. However, it has been known that an organic thin film introduced on a glass surface via a silane reaction is not stable in a buffer solution at a high temperature. (Anal. Chem. 2004, 76, 1778-1787). Its instability in a buffer solution at a high temperature was confirmed again in this experiment but it was found that the thermal stability of the organic layer comprising the dendron was much higher than that of the organic layer not modified with the dendron. In addition, the dendron-modified surface provides sufficient intervals between the immobilized biomolecules, thereby allowing the immobilized biomolecules to interact smoothly with other biomolecules in the solution. Therefore, the polynucleotide synthesis such as DNA or RNA synthesis, DNA or RNA chain extension, PCR, RT-PCR, random priming nucleic acid synthesis, or the other similar polynucleotide synthesis, chain extension, or any amplification method can be carried out on the dendron-modified surface successfully and efficiently.

Another present invention is directed to a dendron-modified surface of a substrate, wherein the dendron-modified surface is obtained by chemically modifying with a dendron in which a plurality of termini of the branched region of the dendron are bound to the surface and a terminus of the linear region of the dendron is functionalized. On the surface, the dendrons may be spaced at regular intervals among the linear functionalized groups. The regular intervals refer to about 0.1 nm to about 100 nm, preferably about 1 nm to about 20 nm, more preferably about 2 nm to about 10 nm, and most preferably about 3 nm to about 5 nm.

The macromolecule and the preparation method of the thin film on a solid surface is disclosed in US Publication No. 20050037413A1, the entire content of which is incorporated hereinto by reference.

The terminus of the branched region of the macromolecule may be functionalized with —COZ, —NHR', —OR', or —PR"$_3$, wherein Z may be a leaving group, wherein R may be an alkyl, wherein R' may be alkyl, aryl, or ether, and R" may be H, alkyl, alkoxy, or O. In particular, COZ may be ester, activated ester, acid halide, activated amide, or CO-imiazoyl; R may be $C_1$-$C_4$ alkyl, and R' may be $C_1$-$C_4$ alkyl. Further, in the above described substrate, the polymer may be a dendron. Still further, the linear region of the polymer may be comprised of a spacer region. And the spacer region may be connected to the branched region via a first functional group. Such first functional group may be without limitation —NH—, —O—, —PH$_2$—, —COO—, —CO— or —S—. Still further, the spacer region may comprise a linker region covalently bound to the first functional group.

In the substrate described above, the linker region may comprise a substituted or unsubstituted alkyl, alkenyl, alkynyl, cycloalkyl, aryl, ether, polyether, ester, or aminoalkyl group. Still further, spacer region may comprise a second functional group. The second functional group may include without limitation NH—, —O—, —PH$_2$—, —COO—, —CO— or —S—. The second functional group may be positioned at the terminus of the linear region and a protecting group may be bound to the terminus of the linear region. The protecting group may be acid labile or base labile.

The surface materials on which macromolecule thin film can be introduced are disclosed in US Publication No. 20050037413A1, the entire content of which is incorporated hereinto by reference. Such materials are used in the present invention.

The substrate described above may consist of semiconductor, synthetic organic metal, synthetic semiconductor, metal, alloy, plastic, silicon, silicate, glass, or ceramic. In particular, the substrate may be, without limitation, a slide, particle, bead, micro-well plate, AFM (atomic force microscope) cantilever or porous material. The porous material may be a membrane, gelatin or hydrogel. And particularly, the bead may be a controlled pore bead.

The present invention uses the method of fixing the target-specific ligand on the terminus of the linear region of the macromolecule disclosed in US publication No. 20050037413A1.

The following Examples 2 and 3 show that the modified surface has sufficient thermal stability in a reaction buffer solution. The Examples 4 to 7 show that the polynucleotide synthesis can be performed efficiently and successfully on the dendron-modified surface at various temperature ranges. As a result, it is demonstrated that the dendron-modified surface is suitable for PCR, RT-PCR, random priming and the other similar amplification methods.

Polymers such as that in Chemical Formula I may be referred to in describing the invention's polymer.

Chemical Formula 1

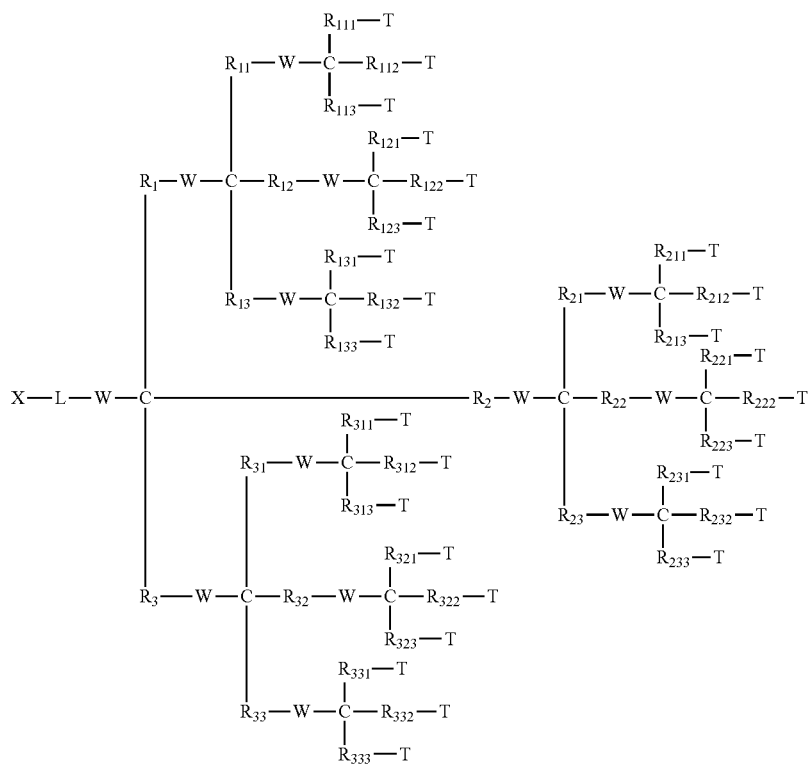

Various K, T, W, L, and X group variables are noted in chemical formula I The polymer may comprise any branched or hyperbranched, symmetrical or asymmetrical polymer. The branched termini of the polymer binds to the substrate preferably by a plurality of termini. The linear end of the polymer may end with a functional group to which a protecting group or a target-specific ligand may be attached. The distance between the probes among the plurality of polymers on a substrate may be from about 0.1 nm to about 100 nm, preferably about 1 nm to about 100 nm, more preferably about 2 nm to about 70 nm, even more preferably about 2 nm to about 60 nm, and most preferably about 2 nm to about 50 nm.

R-Groups

In Formula I, the polymer generally includes a branched section, wherein a plurality of the ends are functionalized to bind to a substrate. Within this branched section, the first generation group of branches Rx (R1, R2, R3) is connected to a second generation group of branches $R_{XX}$ (R11, R12, R13, R21, R22, R23, R31, R32, R33) by a functional group, W. The second gene ration group of branches is connected to a third generation group of branches Rxxx (R111, R112, R113, R121, R122, R123, R131, R132, R133, R211, R212, R213, R221, R222, R223, R231, R232, R233, R311, R312, R313, R321, R322, R323, R331, R332, R333) by a functional group W. And a further fourth generation may be connected to the third generation branches in like fashion. The terminal R group is functionalized so that it is capable of binding to the substrate.

The R groups of all generations may be the same or different. Typically, the R group may be a repeating unit, a linear or branched organic moiety, such as but not limited to alkyl, alkenyl, alkynyl, cycloalkyl, aryl, ether, polyether, ester, aminoalkyl, and so on. However, it is also understood that not all of the R groups need to be the same repeating unit. Nor do all valence positions for the R group need be filled with a repeating unit. For instance, in the first generation branch, $R_x$, $R_1$, $R_2$, $R_3$ all of the R groups at this branch level may be the same repeating units. Or, $R_1$ may be a repeating unit, and $R_2$ and $R_3$ may be H or any other chemical entity. Or, $R_2$ may be a repeating unit, and $R_1$ and $R_3$ may be H or any other chemical entity. Likewise, for the second and third generation branches, any R group may be a repeating unit, H or any other chemical entity.

Thus, a variety of shapes of polymers may be made in this way, for instance, if $R_1$, $R_{11}$, $R_{111}$, $R_{112}$ and $R_{113}$ are the same repeating units, and all other R groups are H's or any number of small neutral molecule or atom, then a fairly long and thin polymer having a branch with three functional group termini for $R_{111}$, $R_{112}$ and $R_{113}$ is made. A variety of other optional chemical configurations are possible. Thus, it is possible to obtain from about 3 to about 81 termini having a functional group capable of binding to a substrate. A preferable number of termini may be from about 3 to about 75, from about 3 to about 70, from about 3 to about 65, from about 3 to about 60, from about 3 to about 55, from about 3 to about 50, from about 3 to about 45, from about 3 to about 40, from about 3 to about 35, from about 3 to about 30, from about 3 to about 27, from about 3 to about 25, from about 3 to about 21, from about 3 to about 18, from about 3 to about 15, from about 3 to about 12, from about 3 to about 9, or from about 3 to about 6.

T-Terminal Group

Terminal groups, T, are functional groups that are sufficiently reactive to undergo addition or substitution reactions. Examples of such functional groups include without limitation, amino, hydroxyl, mercapto, carboxyl, alkenyl, allyl, vinyl, amido, halo, urea, oxiranyl, aziridinyl, oxazolinyl, imidazolinyl, sulfonato, phosphonato, isocyanato, isothiocyanato, silanyl, and halogenyl.

W-Functional Group

In Formula I, W may be any functional group that may link a polymer to another (or any other divalent organic) moiety, such as but not limited to ether, ester, amide, ketone, urea, urethane, imide, carbonate, carboxylic acid anhydride, carbodiimide, imine, azo group, amidine, thiocarbonyl, organic sulphide, disulfide, polysulfide, organic sulphoxide, sulphite, organic sulphone, sulphonamide, sulphonate, organic sulphate, amine, organic phosphorous group, alkylen, alkyleneoxide, alkyleneamine and so on.

L-Spacer or Linker Group

In Chemical Formula 1, the linear portion of the polymer may include a spacer domain comprised of a linker region optionally interspersed with functional groups. The linker region may be comprised of a variety of polymers. The length of the linker may be determined by a variety of factors, including the number of branched functional groups binding to the substrate, strength of the binding to the substrate, the type of R group that is used, in particular, the type of repeating unit that is used, and the type of the protecting group or target nucleotide that is to be attached at the apex of the linear portion of the polymer. Therefore, it is understood that the linker is not to be limited to any particular type of polymer or to any particular length.

However, as a general guideline, the length of the linker may be from about 0.5 nm to about 20 nm, preferably, about 0.5 nm to about 10 nm, and most preferably about 0.5 nm to about 5 nm.

The chemical construct of the linker may include without limitation, a linear or branched organic moiety, such as but not limited to substituted or unsubstituted alkyl, alkenyl, alkynyl, cycloalkyl, cycloalkenyl, aryl, ether, polyether, ester, aminoalkyl, polyalkenylglcol and so on. The linker may further include functional groups such as those described above, and as such is not limited to any particular structure. The linker group functionalized at the tip may comprise a protective group.

X-Protecting Group

The choice of protecting group depends on numerous factors such as the desirability of acid- or base-lability. Therefore, the invention is not limited to any particular protecting group so long as it serves the function of preventing the reaction of the functional group with another chemical entity, and that it is capable of being stripped under desired specified conditions. A list of commercially available protecting groups may be found in the Sigma-Aldrich (2003) Catalog, the contents of which as it relates to the disclosure of protective groups is incorporated by reference herein in its entirety.

In general, in one aspect of the invention, the protecting groups used in the present invention may be those that are used in the sequential addition of one or more amino acids or suitably protected amino acids to a growing peptide chain.

Normally, either the amino or carboxyl group of the first amino acid is protected by a suitable protecting group.

In a particularly preferred method, the amino function is protected by an acid or base sensitive group. Such protecting groups should have the properties of being stable to the conditions of linkage formation, while being readily removable without destruction of the growing branched/linear polymer. Such suitable protecting groups may be without limitation 9-fluorenylmethyloxycarbonyl (Fmoc), t-butyloxycarbonyl (Boc), benzyloxycarbonyl (Cbz), biphenylisopropyl-oxycarbonyl, t-amyloxycarbonyl, isobornyloxycarbonyl, (a,a)-dimethyl-3,5-dimethoxybenzyloxycarbonyl, O-nitrophenylsulfenyl, 2-cyano-t-butyloxycarbonyl, and the like.

Particularly preferred protecting groups also include 2,2,5,7,8-pentamethylchroman-6-sulfonyl (pmc), p-toluenesulfonyl, 4-methoxybenzenesulfonyl, adamantyloxycarbonyl, benzyl, o-bromobenzyloxycarbonyl, 2,6-dichlorobenzyl, isopropyl, t-butyl (t-Bu), cyclohexyl, cyclophenyl and acetyl (Ac), 1-butyl, benzyl and tetrahydropyranyl, benzyl, p-toluenesulfonyl and 2,4-dinitrophenyl.

In the addition method, the branched termini of the linear/branched polymer is attached to a suitable solid support. Suitable solid supports useful for the above synthesis are those materials which are inert to the reagents and reaction conditions of the stepwise condensation-deprotection reactions, as well as insoluble in the media used.

The removal of a protecting group such as Fmoc from the linear tip of the branched/linear polymer may be accomplished by treatment with a secondary amine, preferably piperidine. The protected portion may be introduced in about 3-fold molar excess and the coupling may be preferably carried out in DMF. The coupling agent may be without limitation O-benzotriazol-1-yl-N,N,N',N'-tetramethyluronium-hexafluorophosphate (HBTU, 1 equiv.) and 1-hydroxybenzotriazole (HOBT, 1 equiv.).

The polymer may be deprotected, either in succession or in a single operation. Removal of the polypeptide and deprotection can be accomplished in a single operation by treating the substrate-bound polypeptide with a cleavage reagent, for example thianisole, water, ethanedithiol and trifluoroacetic acid.

The substrate may be any solid surface to which the branched/linear polymer may bind through either covalent or ionic bond. The substrate may be functionalized so that binding may occur between the branched termini of the branched/linear polymer. The surface of the substrate may be a variety of surfaces according to the needs of the practitioner in the art. Preferably, the substrate may be a glass slide. Other substrates may include membrane filters such as but not limited to nitrocellulose or nylon. The substrate may be hydrophilic or polar, and may possess negative or positive charge before or after coating.

The type of dendron and its preparation method is specifically disclosed in US Publication No. 20050037413A1, which is incorporated herein by reference.

Reaction scheme 1 shows the synthesis of a dendron. Various starting materials, intermediate compounds, and dendron compounds can be used, wherein "X" may be any protecting group, including anthracenemethyl (A), Boc, Fmoc, Ns and so forth.

Reaction scheme 1

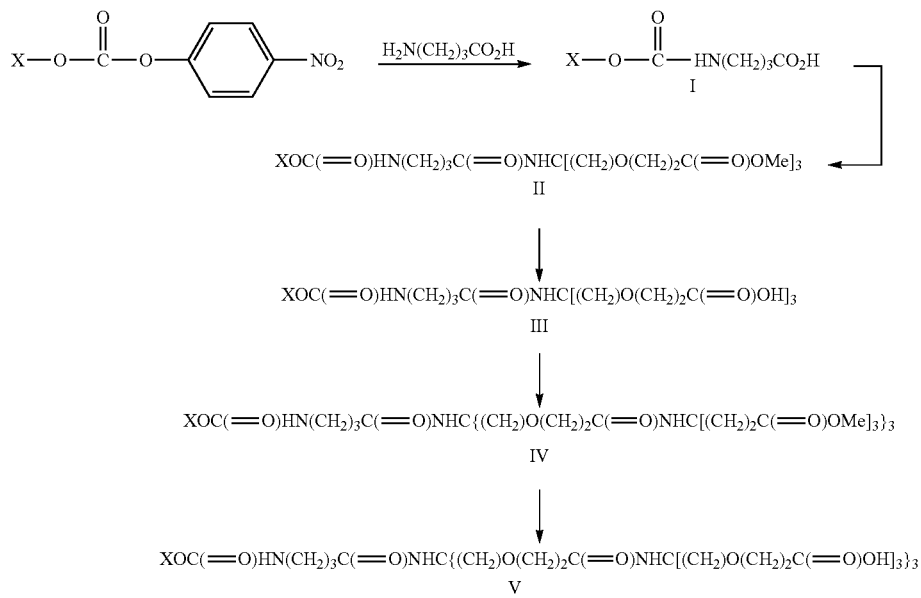

A second generation branch dendron having surface reactive functional groups at the branch termini may be used, which self assembles and provides appropriate spacing among themselves. Previous studies showed that multiple ionic attractions between cations on a glass substrate and anionic carboxylates at the dendron's termini successfully generated a well-behaved monolayer, and guaranteed an inter-ligand space of over 24 Å (Hong et al., Langmuir 18, 2357-2365 (2003)). To facilitate deprotection and increase the deprotected apex amine's reactivity, the structure was modified. Also, covalent bond formation between the dendron's carboxylic acid groups and the surface hydroxyl groups is as effective as ionic attraction, while also providing enhanced thermal stability. Moreover, an oligoetheral interlayer was effective for suppressing non-specific oligonucleotide binding.

The hydroxylated substrate was prepared by using a previously reported method (Maskis et al., Nucleic Acids Res. 20, 1679-1684 (1992)). Substrates including oxidized silicon wafer, fused silica, and glass slide, were modified with (3-glycidoxypropyl)methyldiethoxysilane (GPDES) and ethylene glycol (EG). The dendron was introduced to the above substrates through a coupling reaction between the dendron's carboxylic acid group and the substrate's hydroxyl group using 1-[3-(dimethylamino)propyl]-3-ethylcarbodiimide hydrochloride (EDC) or 1-3-dicyclohexylcarbodiimide (DCC) in the presence of 4-dimethylaminopyridine (DMAP) (Boden et al., J. Org. Chem. 50, 2394-2395 (1985); Dhaon et al., J. Org. Chem. 47, 1962-1965 (1982)). The increase in thickness after dendron introduction was 11±2 Å, which was comparable to the previous value observed for the ionic bonding (Hong et al., Langmuir 19, 2357-2365 (2003)).

After modification with di(N-succinimidyl)carbonate (DSC) according to a previously established method (Beier et al., Nucleic Acids Res. 27, 1970-1977 (1999)), probe oligonucleotides were immobilized onto the activated surface of glass slide by spotting 50 mM sodium bicarbonate buffer (10% dimethylsulfoxide (DMSO), pH 8.5) solution of the appropriate amine-tethered oligonucleotide (20, uM) using a Microsys 5100 Microarrayer (Cartesian Technologies, Inc.) in a class 1,000 clean room. Typically, for substrates with a reactive amine surface group, a thiol-tethered oligonucleotide and a heterobifunctional linker such as succinimidyl 4-maleimido butyrate (SMB) or sulphosuccinimidyl-4-(N-maleimidomethyl)cyclohexane-1-carboxylate (SSMCC) are employed (Oh et al., Langmuir 18, 1764-1769 (2002); Frutos et al., Langmuir 16, 2192-2197 (2000)). In contrast, because the dendron-modified surface guarantees a certain distance among the amine functional groups, use of homobifunctional linkers such as DSC is not problematic. As a result, an amine-tethered oligonucleotide can be utilized for spotting. Unless cost effectiveness is important, use of easily oxidized thiol-tethered oligonucleotide should be avoided, although it is possible that such thiol-tethered oligonucleotides may be useful under certain conditions.

To improve the recognition efficiency between complementary DNA strands at the single molecular level, DNA oligomers was immobilized onto a nanoscale-controlled dendron surface. The surface seemed to be ideal to increase the efficiency since the mesospacing existing in the dendron relieved the immobilized DNA from the steric hindrance (B. J. Hong, S. J. Oh, T. O. Youn, S. H. Kwon, J. W. Park, Langmuir 21, 4257, 2005). Either glycidylpropyldiethoxymethylsilane (or GPDES) or N-(3-(triethoxysilyl)propyl)-O-polyethyleneoxide urethane (or TPU) was employed to generate a sublayer, and the dendron (9-anthrylmethyl N-({[tris({2-[({tris[(2-carboxyethoxy)methyl]methyl}amino) carbonyl]ethoxy}methyl)methyl]amino}carbonyl) propylcarbamate) (or 9-acid) was immobilized onto them. Previously, mesospacing between the dendrons on the GPDES-modified surface was 32 Å on average (B. J. Hong, S. J. Oh, T. O. Youn, S. H. Kwon, J. W. Park, Langmuir 21, 4257, 2005). In the case of TPU, an absorption peak observed at 257 nm arising from the anthracene moiety of the pristine dendron was one half of that in the GPDES case. Therefore it is suggested that the spacing of the dendron is larger than 32 Å in the TPU case. After deprotection of the anthracene protecting group, the amine group was activated with di(N-succinimidyl)carbonate, and eventually an amine tethering oligonucleotide was immobilized.

The present invention is further explained in more detail with reference to the following examples. The scope of the present invention, however, is not limited to the following examples.

EXAMPLE 1

Preparation of Dendron-Modified Substrate

The two types of the modification (9-acid/GPDES substrate and 9-acid/TPU substrate) were employed for the substrate by using the two silane agents GPDES and TPU.

Example 1.1

Materials

The silane coupling reagents, (3-glycidoxypropyl)methyldiethoxysilane (GPDES) and N-(3-(triethoxysilyl)propyl)-O-polyethyleneoxide urethane (TPU) was purchased from Gelest Inc. and all other chemicals were of reagent grade from Sigma-Aldrich. Reaction solvents for the silylation are anhydrous ones in Sure/Seal bottles from Aldrich. All washing solvents for the substrates are of HPLC grade from Mallinckrodt Laboratory Chemicals. Glass slides (2.5×7.5 cm) were purchased from Corning Co. Ultrapure water (18 M Ω/cm) was obtained from a Milli-Q purification system (Millipore).

Example 1.2

Cleaning the Substrates

Glass slide as a substrate was immersed into Piranha solution (conc. H2SO4:30% H2O2=7:3 (v/v)) and a reaction bottle containing the solution and the substrates was sonicated for an hour. The plates were washed and rinsed thoroughly with a copious amount of deionized water after the sonication. The clean substrates were dried in a vacuum chamber (30-40 mTorr) for the steps to be followed.

Example 1.3

Preparing the Hydroxylated Substrates

The above clean substrates were soaked in 200 ml toluene solution with 1.0 ml (3-glycidoxypropyl)methyldiethoxysilane (GPDES) for 2 hours. After the self-assembly, the substrates were washed with toluene briefly, placed in an oven, and heated at 110° C. for 30 minutes. The plates were sonicated in toluene, toluene-ethanol (1:1 (v/v)), and ethanol in a sequential manner for 3 min at each washing step. The washed plates were dried in a vacuum chamber (30-40 mTorr). GPDES-modified substrates were soaked in a neat ethylene glycol (EG) solution at 120° C. for 2 h. After cooling, the substrates were sonicated in D.I water and ethanol in a sequential manner each for 3 min. The washed plates were dried in a vacuum chamber (30-40 mTorr).

Clean slide glass was immersed into anhydrous toluene (200 mL) containing N-(3-(triethoxysilyl)propyl)-O-polyethyleneoxide urethane (TPU) as a silane coupling agent (1.0 mL) under nitrogen atmosphere, and placed in the solution for 6 h. After silylation, the substrates were washed with toluene, baked for 30 min at 110° C. The substrates were immersed in toluene, toluene-ethanol (1:1 (v/v)), and ethanol in a sequential manner, and they were sonicated for 3 min in each washing solution. The substrates were rinsed thoroughly with toluene and methanol in a sequential manner. Finally the substrates were dried under vacuum (30-40 mTorr).

Example 1.4

Preparing the Dendron-Modified Substrates

The above hydroxylated substrates were immersed into a methylene chloride solution dissolving (9-anthrylmethyl N-({[tris({2-[({tris[(2-carboxyethoxy)methyl] methyl}amino)carbonyl]ethoxy}methyl)methyl] amino}carbonyl)propylcarbamate) (or 9-acid) (0.5 mM) and a coupling agent, 1-[-3-(dimethylamino)propyl]-3-ethylcarbodiimide hydrochloride (EDC) or 1,3-dicyclohexylcarbodiimide (DCC) (5 mM) in the presence of 4-dimethylaminopyridine (DMAP) (4 mM). After 2 h at room temperature, the plates were sonicated in methanol, water, and ethanol in the respective sequence each for 3 minutes. The washed plates were dried in a vacuum chamber (30-40 mTorr) for the step to be followed.

Example 1.5

Preparing the NHS-Modified Substrates

The dendron-modified substrates were immersed into a methylene chloride solution with 0.1 M trifluoroacetic acid (TFA). After 1 hour, they were again soaked in a methylene chloride solution with 1% (v/v) triethylamine(TEA) for 10 minutes. The plates were sonicated in methylene chloride and ethanol each for 3 minutes. After being dried in a vacuum chamber, the deprotected substrates were incubated in acetonitrile solution with di(N-succinimidyl)carbonate (DSC) (12.5 mM) and 0.1% (v/v) DIPEA. After 4 hours of reaction, the plates were placed in a stirred dimethylformamide solution for 20 min and then were washed briefly with ethanol. The washed plates were dried in a vacuum chamber (30-40 mTorr) for the step to be followed.

EXAMPLE 2

Thermal Stability of the Immobilized DNAs on Dendron-Modified Surface

To test the thermal stability of the biomolecules on several different surfaces, Silanated slide, Dendron/EG/GPDES slide, and Dendron/TPU slide were used in this example. This example is to compare how DNA molecules immobilized on the dendron-modified surface of the present invention and on the aminosilane treated surface used in the conventional art were maintained stably in buffer solution at a high temperature. The Silanated slide (TeleChem International, Inc) which was treated with aminosilane was used as a comparative example. Dendron/EG/GPDES slide, and Dendron/TPU slide were the same as those of Example 1. The oligonucleotides used in this example included an amino group at 3' end and Cy3 dye at 5' end as follows:

5'Cy3-TTT TTT TTT T-NH$_2$-3' (SEQ ID NO: 1)

A PCR buffer solution (50 mM KCl, 10 mM Tris-HCl, and 1.5 mM MgCl$_2$ (pH 7.4)) was used as the buffer solution for measuring the thermal stability.

The oligonucleotides including a fluorescent dye were spotted on the dendron-modified surface of Example 1 with a microarrayer and the surface was incubated for a sufficient time to allow the oligonucleotides to be immobilized on the surface. Unreacted oligonucleotides were removed by rinsing with a washing buffer. The glass slide was dried, and then the fluorescence signal of the immobilized oligonucleotides was measured using a laser fluorescent scanner.

The glass slide showing the fluorescent signal was immersed in a PCR buffer solution at a temperature of 92-98° C. for 5 minutes, washed with deionized water and dried before the fluorescence signal of the immobilized oligonucleotides was measured using a laser fluorescent scanner. Again, the glass slide showing the fluorescent signal was immersed in a PCR buffer solution at a temperature of 92-98° C. for 5 minutes, washed with deionized water and dried before the fluorescence signal of the immobilized oligonucleotides was measured using a laser fluorescent scanner. The repetitive experiments as described above were carried out and then the intensity of fluorescent signal was analyzed for different repetition numbers.

It has been known that an organic thin film introduced on a glass surface by using the silane reaction is not stable in a buffer solution at a high temperature. (Anal. Chem. 2004, 76, 1778-1787). Of course, its instability in a buffer solution at a high temperature was confirmed again in this experiment but it was found that the thermal stability of the dendron-modified organic layer was much higher than that of the organic layer without being modified with the dendron. In addition, the dendron-modified surface provides sufficient intervals between the immobilized biomolecules, thereby allowing the immobilized biomolecules to interact smoothly with other biomolecules in solution.

Figure 3A:
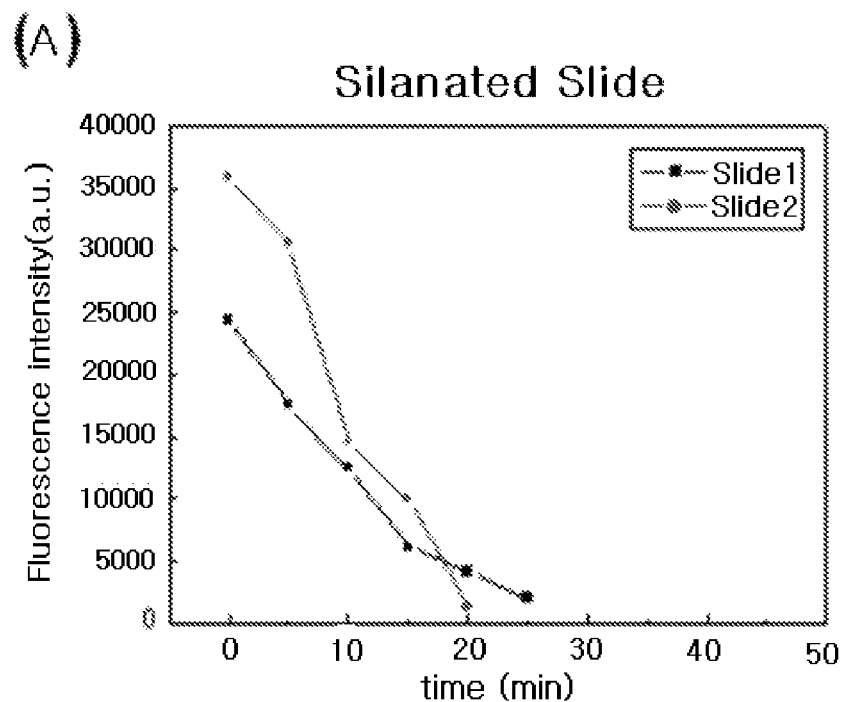
FIG. 3 shows the thermal stability of the silanated slide. (A) is the graph and (B) is the fluorescent image showing thermal stability, wherein the numerical value below each image means the number of surface treatment with PCR solution of high temperature.
Figure 3B:
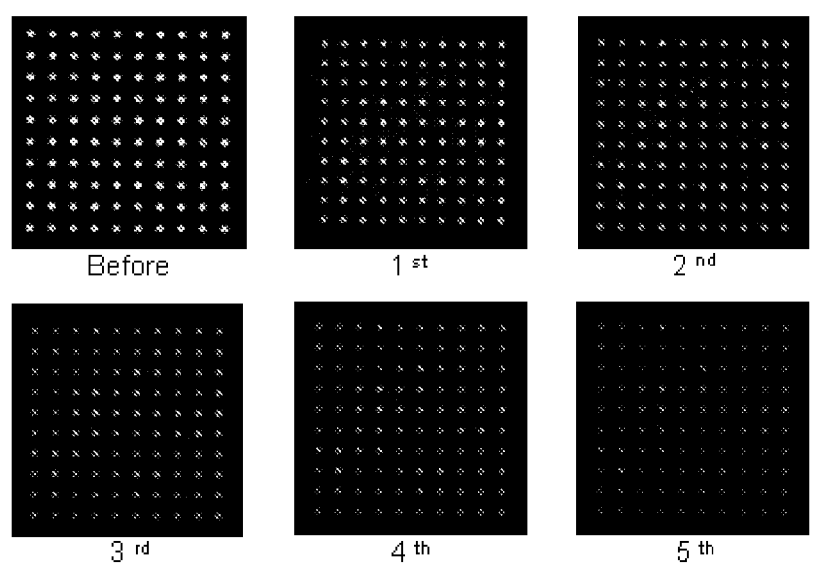

The Silanated slide used as a comparative example showed steep decrease of the fluorescent intensity as the repetition number increased (FIG. 3A and FIG. 3B). However, although the dendron-modified surface showed the decreased intensity of the fluorescent signal, the amount of decrease was significantly smaller compared to that of the Silanated slide (FIG. 4A and FIG. 4B).

Figure 4A:
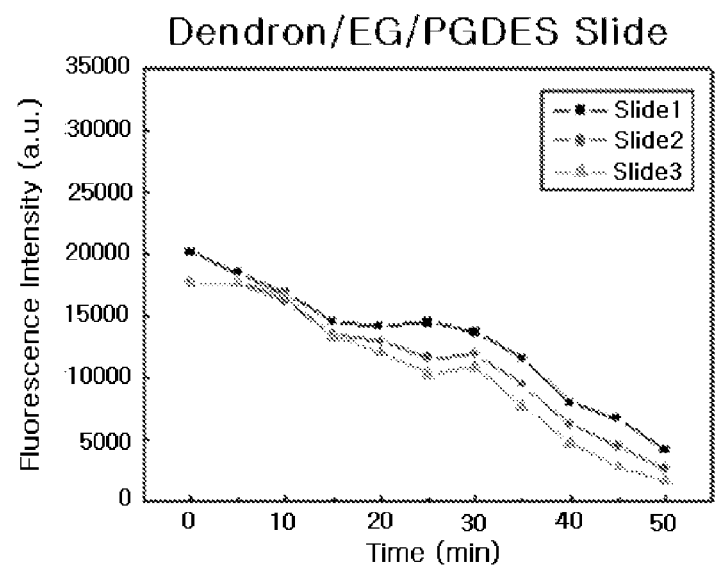
FIG. 4 shows the thermal stability of Dendron/(ethylene glycol(EG)/(3-glycidoxypropyl)methyldiethoxysilane (GP-DES) slide. (A) is the graph and (B) is the fluorescent image showing thermal stability, wherein the numerical value below each image means the number of surface treatment with PCR solution of high temperature.
Figure 4B:
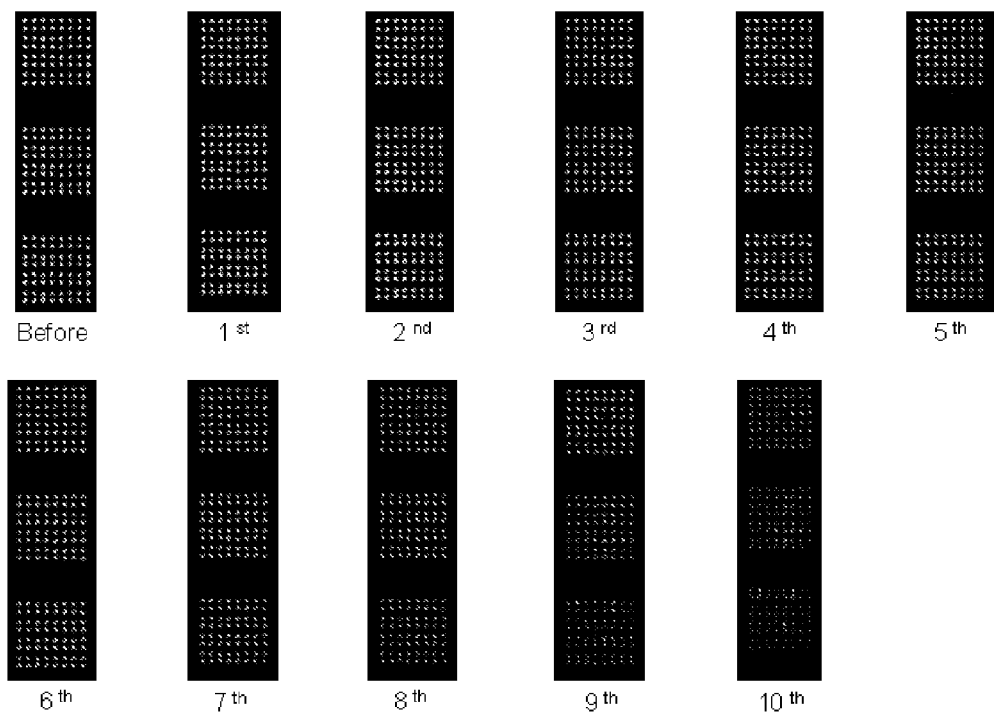
Figure 5A:
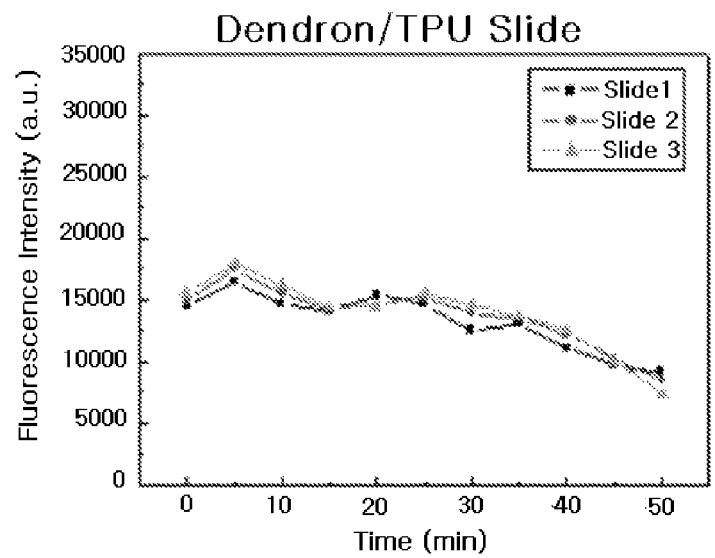
FIG. 5 represents the thermal stability of Dendron/TPU slide. (A) is the graph and (B) is the fluorescent image showing thermal stability, wherein the numerical value below each image means the number of surface treatment with PCR solution of high temperature.
Figure 5B:
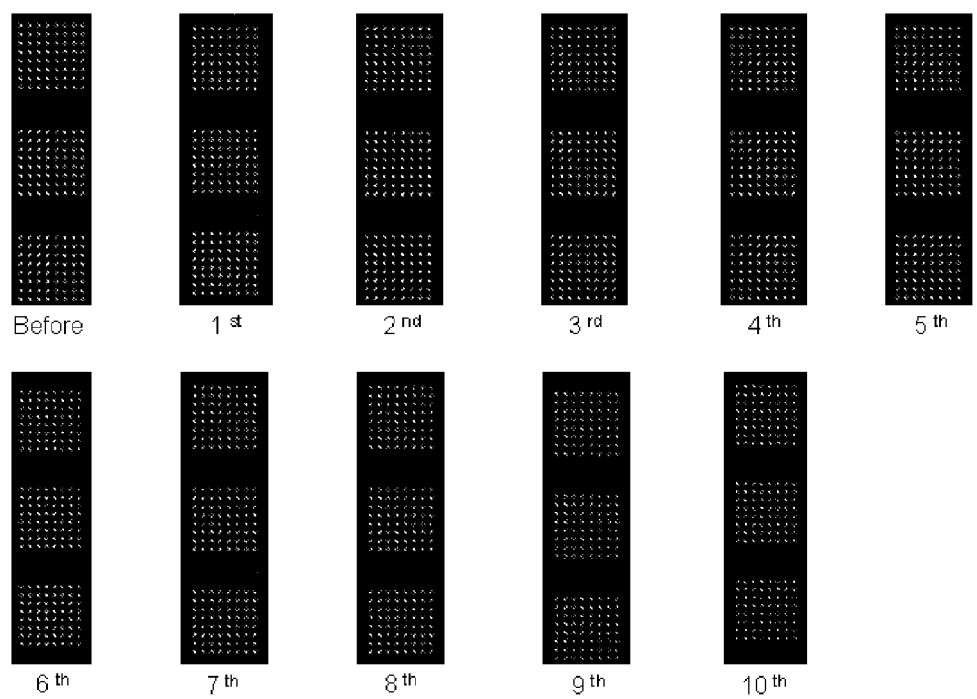
Figure 6:
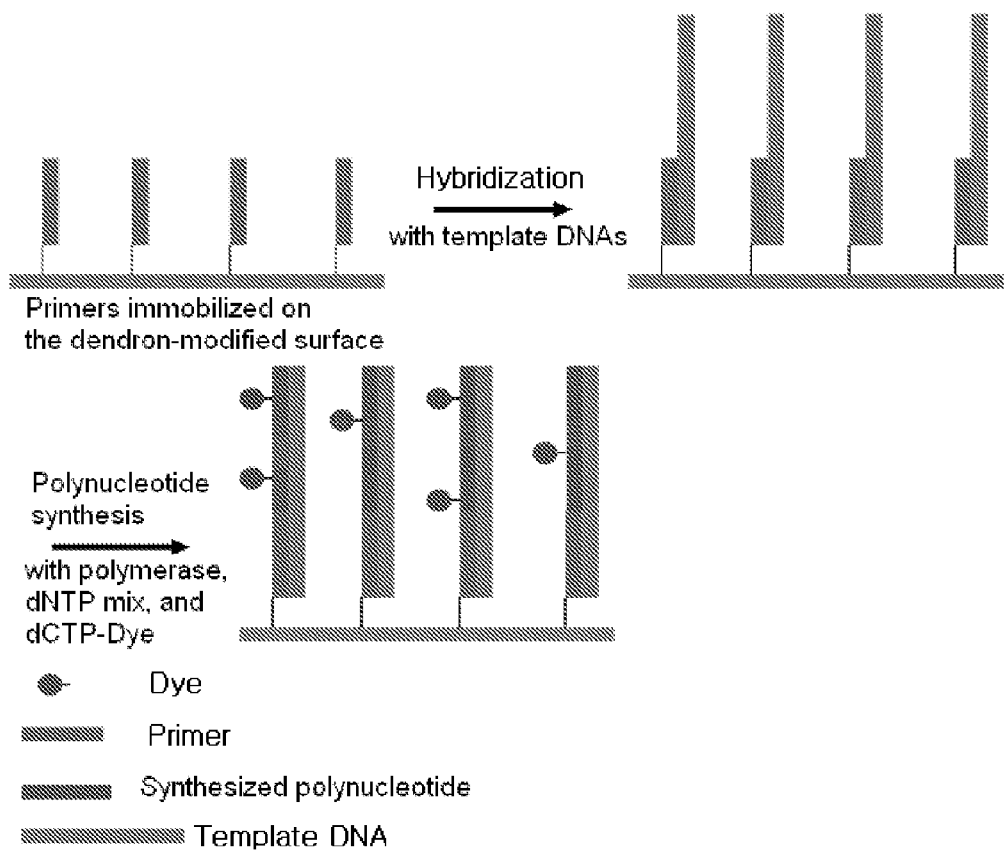
FIG. 6 is a schematic view showing the polynucleotide synthesis following the binding between the primer DNA and template DNA.
Figure 7:
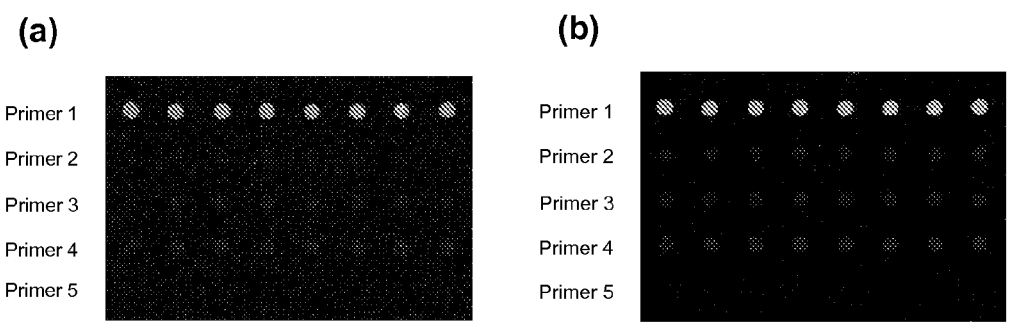
FIG. 7 is a fluorescent image of DNA microarray obtained from the polynucleotide synthesis by using Klenow DNA polymerase I: (A) Cy5 fluorescent image and (B) Cy3 fluorescent image.
Figure 8:
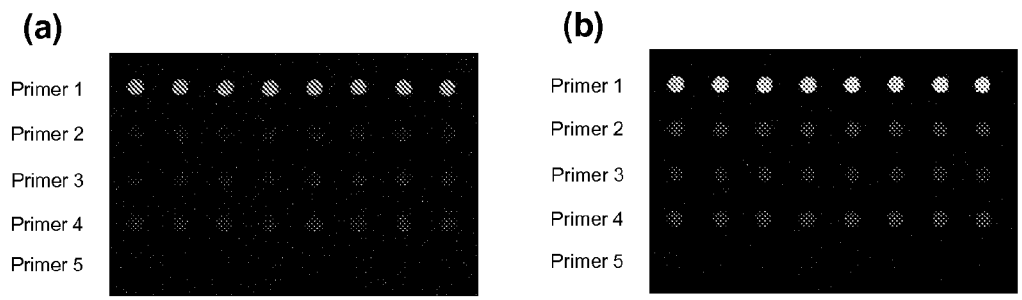
FIG. 8 is a fluorescent image of DNA microarray obtained from the polynucleotide synthesis by using Tag polymerase: (A) Cy5 fluorescent image and (B) Cy3 fluorescent image.

In addition, in the preparation method of the dendron-modified solid surface, the solid surface treated with TPU (N-(3-(triethoxysilyl)propyl)-o-polyethylene oxide urethane) (FIG. 5A and FIG. 5B) was shown to be thermally more stable than those treated with GPDES ((3-glycidoxypropyl)methyldiethoxysilane) and ethylene glycol (FIG. 4A and FIG. 4B). It suggested that the TPU organic thin film block off the salts in buffer solution approaching the glass slide surface efficiently, and minimized the damage of Si—O bond.

EXAMPLE 3

Thermal Cycle Reaction with Enzymes on a Dendron-Modified Surface

Based on the thermal stability test in Example 2, PCR, RT-PCR or the other similar thermal cycles could be performed on the dendron-modified surface by carrying out a general PCR and RT-PCR procedures on the surface.

As a comparative example, the Silanated slide (TeleChem International, Inc.) treated with an aminosilane compound was used in this example. Dendron/EG/GPDES slide and Dendron/TPU slide were the same as those of Example 1. The Taq DNA polymerase generally used in PCR was used in this example. The buffer solution for Taq DNA polymerase included 40 mM KCl, 10 mM Tris-HCl, 1.5 mM $MgCl_2$, but could be different according to the enzymes used. The buffer solution for DNA polymerase can be adjusted depending on the enzyme used.

The oligonucleotides used in this example included an amino group at 3' end and Cy3 dye at 5' end as follows:

5'-Cy3-ACA AGC ACA GTT AGG-$NH_2$-3' (SEQ ID NO: 2)

The oligonucleotides including a fluorescent dye were spotted on the dendron-modified surface of Example 1 with a microarrayer and the surface was incubated in a sufficient time to allow the oligonucleotides to be immobilized on the surface. Unreacted oligonucleotides were removed by rinsing with a washing buffer. The glass slide was dried, and then the fluorescence signal of the immobilized oligonucleotides was measured using a laser fluorescent scanner.

The glass slide was immersed in a buffer solution containing 100 μM dATP, 100 μM dTTP, 100 μM dCTP, 100 μM dGTP, and Taq DNA polymerase, and heated at 94° C. for 2 minutes. Then, the heating cycle which was at 94° C. for 20 seconds, at 60° C. for 20 seconds, and at 72° C. for 20 seconds was repeated at 20 cycles sequentially, and then was at 72° C. for 7 minutes for the last step. The glass slide was washed with deionized water, dried, and then the fluorescence signal of the immobilized oligonucleotides was measured using a laser fluorescent scanner to compare the intensities of fluorescent signals in the samples obtained before and after PCR.

As a result, the comparative example of Silanated slide showed 20,000 of fluorescent intensity before PCR but showed a steep decrease of the intensity to 2,000 after PCR. On the other hand, dendron/TPU slide showed much smaller decrease of the fluorescent intensity from 15,000 before PCR to 11,000. This result was consistent with that of thermal stability obtained in Example 2, and represented that the dendron-modified surface provided the higher stability of an immobilized biomolecule and a coated organic layer on a surface than the general silanated slide. Thus, the result confirmed that PCR, RT-PCR and other thermal cycle procedures could be carried out efficiently on the dendron-modified surface.

EXAMPLE 4

4.1. Immobilization of Primers on a Dendron-Modified Surface

In this example, a polynucleotide was synthesized successfully on the dendron modified surface by a polymerase. The dendron-modified surface used in this Example was the same as that of Example 1, and the oligonucleotides immobilized on the surface were as follows.

TABLE 1

| NAME | SEQUENCE(5' to 3') | SEQ ID NO |
|---|---|---|
| Primer 1 | 5'-$NH_2$-gatcaccagcggcatcgag-3' | 3 |
| Primer 2 | 5'-$NH_2$-gatcaccaccggcatcgag-3' | 4 |
| Primer 3 | 5'-$NH_2$-cgatcaccaacggcatcgag-3' | 5 |
| Primer 4 | 5'-$NH_2$-cgatcaccatcggcatcgag-3' | 6 |
| Primer 5 | 5'-$NH_2$-atcacccgcggcatcga-3' | 7 |

The oligonucleotide as described in Table 1 are markers to detect the katG gene of *Mycobacterium tuberculosis*, and particularly mutated kat G gene in codon 315. Primer 1 is designed for detecting wild type *Mycobacterium tuberculosis*, and Primers 2 to 5 are designed for detecting each mutant type. Primers 1 to 5 had $NH_2$ group on their 5'-end. The template DNA to which the immobilized oligonucleotides on a dendron-modified surface bind is isolated from *Mycobacterium tuberculosis*, the 315 codon-containing gene fragment of isolated whole gene is only amplified with PCR where the dCTP-Cy5 was added to be labeled. The template DNA has a length of about 200 base pairs. Klenow DNA polymerase I and Tag polymerase can be used at a temperature of 35-40° C. and 60-95° C., respectively.

FIG. 6 is a schematic view showing the polynucleotide synthesis on a dendron-modified surface following the binding between the primer DNA and the template DNA. Firstly, the primers were spotted on the dendron-modified surface with a microarrayer, and the surface was incubated in a sufficient time for the oligonucleotides to be immobilized on the surface. Unreacted primers were removed by rinsing with a washing buffer. The glass slide was then dried. The obtained DNA microarray was hybridized with the template DNA at 45-65° C. for 1-4 hours, and the unhybridized template DNAs were removed by washing with a buffer solution, and then the surface including the DNA microarray was dried.

4.2. Polynucleotide Synthesis on a Dendron-Modified Surface by Using Klenow DNA Polymerase I The obtained DNA microarray was incubated in a reaction buffer solution of Klenow DNA polymerase I at 37° C. for 5 minutes in order to sufficiently soak the DNA microarray on the slide, and then incubated with addition of a buffer solution including Klenow DNA polymerase 1,100 μM dATP, 100 μM dTTP, 100 μM dGTP, 50 μM dCTP, and 50 μM dCTP-Cy3 at 37° C. for 30 minutes. The DNA microarray was washed with PBS solution, and dried before the fluorescent signal of DNA microarray was measured.

FIG. 7 is a fluorescent image of the DNA microarray obtained from the polynucleotide synthesis by using Klenow DNA polymerase I: (A) Cy5 fluorescent image which showed the fluorescent signal of the Cy5-labeled Template DNA hybridized with primers, and (B) Cy3 fluorescent image which showed the fluorescent signal of the dCTP-Cy3 incorporated into the synthesized polynucleotide on the dendron-modified surface. The result of FIG. 7A represented that the hybridization between the primers and template DNA on the dendron-modified surface occurred with high selectivity. The result of FIG. 7B confirmed that the polynucleotide synthesis on the solid surface by using Klenow DNA polymerase I was performed successfully. As shown in FIGS. 7A and 7B, the hybridization and polynucleotide synthesis performed by using Primer 1 which did not include a mismatched base, and Primer 2 to 5 which included one mismatched base pair showed that only Primer 1 provided complete hybridization with the template DNA and the polynucleotide synthesis on the dendron-modified surface. Such result also suggested that the dendron-modified surface of the present invention can ensure high selectivity to complementary DNA and mismatched DNA during a polynucleotide synthesis process.

4.3. Polynucleotide Synthesis on Dendron-Modified Surface by Using Tag DNA Polymerase The DNA microarray after hybridization with template DNA was immersed in Tag DNA polymerase reaction buffer solution, and incubated at 72° C. for 5 minutes to allow the upper side of the DNA microarray on the slide to be wet sufficiently. The DNA microarray was immersed in a buffer solution containing Tag DNA polymerase, 100 μM dATP, 100 μM dTTP, 100 μM dGTP, 50 μM dCTP, and 50 μM dCTP-Cy3, and was incubated at 72° C. for 5 minutes. Then, the microarray was washed with PBS solution, and dried before its fluorescence was measured.

FIG. 8 is a fluorescent image of DNA microarray obtained from the polynucleotide synthesis by using Taq polymerase: (A) Cy5 fluorescent image which showed the fluorescent signal of the Cy5-labeled Template DNA hybridized with primers, and (B) Cy3 fluorescent image which showed the fluorescent signal of the dCTP-Cy3 incorporated into the synthesized polynucleotide on the dendron-modified surface.

The result of FIG. 8A represented that the hybridization between the primers and the template DNA on the dendron-modified surface occurred with high selectivity. The result of FIG. 8B confirmed that the polynucleotide synthesis on the solid surface by using Taq polymerase was performed successfully.

As shown in FIG. 8A and FIG. 8B, in the case of the polynucleotide synthesis by using Primer 1 which does not include a mismatched base, and Primers 2 to 5 which include 1 mismatched base, the hybridization and polynucleotide synthesis results showed that only Primer 1 completely hybridized with the template DNA, and thus synthesized the polynucleotide on the dendron-modified surface. Thus, the dendron-modified surface showed high selectivity to complementary DNA and mismatched DNA during a polynucleotide synthesis process

EXAMPLE 5

PCR Reaction on a Dendron-Modified Surface Tethered with a Polymerase

In this example, a PCR reaction can be performed successfully on the dendron modified surface tethered with a polymerase. The dendron-modified surface used in this Example is the same as that of Example 1, and the polymerase can be immobilized on the surface using two methods. One is to directly immobilize a polymerase on the surface because it has amino groups at some of its side chain or N terminal position. Another is to immobilize a polymerase on the surface using GSH (glutathione) and GST (glutathione-S-transferase) coupling method, wherein a GMBS (4-maleimidobutyric acid-N-hydroxysuccinimide ester) and GSH is introduced onto a dendron-modified surface sequentially, and then GST-fused polymerase is coupled with GSH tethered on the dendron-modified surface.

The dendron-modified surface is incubated in a buffer solution including Tag polymerase at 25-37° C. for 0.5-1 hour to allow the polymerase to be immobilized on the surface. The surface is rinsed with a washing buffer to free polymerases which are not immobilized on the surface. The surface is first incubated in a reaction buffer solution containing primers, template DNA, 100 μM dATP, 100 μM dTTP, 100 μM dGTP, 50 μM dCTP, and 50 μM dCTP-Cy3 at 25° C. for 5 minutes to allow the polymerase-tethered surface to be wet sufficiently. A template DNA is the same as that of Example 4 and primers is the below.

```
                                        (SEQ ID NO: 8)
Primer 6-forward: 5'-CTGGAAGAGCTCGTATGGCACC-3'

(SEQ ID NO: 9)
Primer 7-reverse: 5'-GCCGTACAGGATCTCGAGGAA-3'
```

After it is heated at 94° C. for 2 minutes, the heating cycle which is at 94° C. for 20 seconds, at 60° C. for 20 seconds, and at 72° C. for 20 seconds is repeated at 20 cycles sequentially, and then it is heated at 72° C. for 7 minutes for the last step.

After this PCR reaction, the solution is collected and the successful PCR reaction is confirmed by a gel electrophoresis tool. In addition, the reaction buffer solution is purified to collect only the synthesized polynucleotides, which is identified by measuring its UV absorbance or fluorescence signal of incorporated dyes.

EXAMPLE 6

PCR Reaction on a Dendron-Modified Surface Tethered with a Template DNA

In this example, a PCR reaction can be performed successfully on the dendron modified surface tethered with a template DNA. The dendron-modified surface used in this Example is the same as that of Example 1 and the template DNA is the same as that of Example 4.

The dendron-modified surface is incubated in a buffer solution including a template DNA at room temperature overnight to allow it to be immobilized on the surface. The surface is rinsed with a washing buffer to free template DNAs which are not immobilized on the surface and then dried. The obtained surface is first incubated in a reaction buffer solution containing primers, Tag polymerase, 100 μM dATP, 100 μM dTTP, 100 μM dGTP, 50 μM dCTP, and 50 μM dCTP-Cy3 at 25° C. for 5 minutes to allow the polymerase-tethered surface to be wet sufficiently. The primers used here are the same as those of Example 5.

After the surface is heated at 94° C. for 2 minutes, the heating cycle which is at 94° C. for 20 seconds, at 60° C. for 20 seconds, and at 72° C. for 20 seconds is repeated at 20 cycles sequentially, and then it is heated at 72° C. for 7 minutes for the last step. After this PCR reaction, the solution is collected and the successful PCR reaction is confirmed by a gel electrophoresis tool. In addition, the reaction buffer solution is purified to collect only the synthesized polynucleotides, which is identified by measuring its UV absorbance or fluorescence signal of incorporated dyes.

EXAMPLE 7

PCR Reaction & Simultaneous Detection of PCR Products on a Dendron-Modified Surface In this example, a PCR reaction is performed successfully on the dendron modified surface and the PCR products are detected simultaneously on the same surface. The dendron-modified surface used in this Example is the same as that of Example 1, and the target-specific ligands which are the oligonucleotides immobilized on the surface and specifically hybridized with PCR products are as follows.

TABLE 2

| NAME | SEQUENCE(5' to 3') | SEQ ID NO |
|---|---|---|
| Ligand 1 | 5'-gatcaccagcggcatcgag-$NH_2$-3' | 10 |
| Ligand 2 | 5'-gatcaccaccggcatcgag-$NH_2$-3' | 11 |
| Ligand 3 | 5'-cgatcaccaacggcatcgag-$NH_2$-3' | 12 |
| Ligand 4 | 5'-cgatcaccatcggcatcgag-$NH_2$-3' | 13 |
| Ligand 5 | 5'-atcacccgcggcatcga-$NH_2$-3' | 14 |

The oligonucleotides as described in Table 2 are markers to detect the katG gene of *Mycobacterium tuberculosis*, and particularly mutated kat G gene in codon 315. Ligand 1 is designed for detecting wild type *Mycobacterium tuberculosis*, and Ligands 2 to 5 are designed for detecting each mutant type. All Ligands had $NH_2$ group on their 3'-end to prevent them from being synthesized during PCR.

Firstly, the Ligands 1 to 5 are spotted on the dendron-modified surface with a microarrayer, and the surface is incubated in a sufficient time for the oligonucleotides to be immobilized on the surface. Unreacted oligonucleotides are removed by rinsing with a washing buffer and then the surface is then dried. The obtained surface is incubated in a reaction buffer solution containing primers, a template DNA, Tag polymerase, 100 μM dATP, 100 μM dTTP, 100 μM dGTP, 50 μM dCTP, and 50 μM dCTP-Cy3. The primers used here are the same as those of Example 5, and the template DNA is a 315 codon-containing whole gene which is isolated from *Mycobacterium tuberculosis*. After the surface is heated at 94° C. for 2 minutes, the heating cycle which is at 94° C. for 20 seconds, at 60° C. for 20 seconds, and at 72° C. for 20 seconds is repeated at 20 cycles sequentially, and then it is incubated at 50-60° C. for 30 minutes. The surface is rinsed with a washing buffer and then dried. The fluorescence signal of the surface is measured using a laser fluorescent scanner to identify the targeted PCR products after PCR.

While the present invention has been described in detail with reference to the preferred embodiments, those skilled in the art will appreciate that various modifications and substitutions can be made thereto without departing from the spirit and scope of the present invention as set forth in the appended claims.

What is claimed is:

1. A method of producing a polynucleotide using a solid phase polymerase chain reaction (PCR), said method comprising:
   (i) contacting a solid substrate comprising a primer that is attached to the solid substrate surface through a linker that is covalently attached to the solid substrate with a solution comprising a polymerase, dNTP or NTP, and a template DNA or RNA under polymerase chain reaction conditions sufficient to produce a polynucleotide that is complementary to the template DNA or RNA;
   (ii) contacting a solid substrate comprising a template DNA or RNA that is attached to the solid substrate surface through a linker with a solution comprising a polymerase, dNTP or NTP, and a primer under polymerase chain reaction conditions sufficient to produce a polynucleotide that is complementary to the template DNA or RNA; or
   (iii) contacting a solid substrate comprising a polymerase that is attached to the solid substrate surface through a linker with a solution comprising a primer, dNTP or NTP, and a template DNA or RNA under polymerase chain reaction conditions sufficient to produce a polynucleotide that is complementary to the template DNA or RNA;

wherein the linker comprises a dendron that comprises a plurality of termini covalently attached to the solid substrate surface and a single linear region that is attached to the primer, the template DNA or RNA, or the polymerase of (i), (ii), or (iii), respectively, and wherein attachment of the linker to the solid substrate provides a significantly higher thermal stability to the PCR conditions such that when the solid substrate is a glass slide, the linker provides more than twice the thermal stability compared to aminosilane treated glass slide.

2. The method of claim 1, wherein solid substrate surface comprises a plurality of linkers.

3. The method of claim 1, wherein the linker is a dendron that comprises a plurality of termini that is attached to the solid substrate surface and a linear region that is attached to the primer, the template DNA or RNA, or the polymerase of (i), (ii), or (iii), respectively.

4. The method of claim 1, wherein the polymerase is selected from the group consisting of DNA polymerase, RNA polymerase, Tag polymerase, polymerase derived from Taq polymerase, Klenow DNA polymerase I, and a reverse transcriptase.

5. The method of claim 1, wherein PCR comprises a real time PCR, or a RT-PCR (reverse transcription PCR).

6. The method of claim 1, wherein the solid substrate comprises semiconductor, synthetic organic metal, synthetic semiconductor, metal, alloy, plastic, silicon, silicate, glass, ceramic, or a combination thereof 7. The method of claim 1, wherein the solid substrate comprises a slide, a particle, a bead, a micro-well, or a porous material.

8. The method of claim 7, wherein the porous material comprises a membrane, a gelatin or a hydrogel.

9. The method of claim 7, wherein the bead is a controlled pore bead.

10. A method for producing a polynucleotide on a solid substrate surface, said method comprising contacting a solid substrate comprising a primer that is attached to the solid substrate surface through a linker that is covalently attached to the solid substrate surface with a solution comprising a polymerase, dNTP or NTP, and template DNA or RNA under conditions sufficient to produce a solid substrate surface bound polynucleotide that is complementary to the template DNA or RNA, wherein the linker comprises a dendron that comprises a plurality of termini covalently attached to the solid substrate surface and a single primer attached linear region, wherein attachment of the linker to the solid substrate provides a significantly higher thermal stability such that when the solid substrate is a glass slide, the linker provides more than twice the thermal stability compared to aminosilane treated glass slide when the solid substrate is repeatedly subjected to PCR buffer solution at temperature of 92-98° C.

11. The method of claim 10, wherein solid substrate surface comprises a plurality of linkers.

12. The method of claim 10, wherein the linker is a dendron that comprises a plurality of termini that is attached to the solid substrate surface and a linear region that is attached to the primer.

13. The method of claim 10, wherein the polymerase is selected from the group consisting of DNA polymerase, RNA polymerase, Tag polymerase, polymerase derived from Taq polymerase, Klenow DNA polymerase I, and a reverse transcriptase.

14. The method of claim 10, wherein said method comprises Polymerase Chain Reaction (PCR), real time PCR, or RT-PCR (reverse transcription PCR).

15. The method of claim 10, wherein the solid substrate comprises semiconductor, synthetic organic metal, synthetic semiconductor, metal, alloy, plastic, silicon, silicate, glass, ceramic, or a combination thereof 16. The method of claim 10, wherein the solid substrate comprises a slide, a particle, a bead, a micro-well, or a porous material.

17. The method of claim 16, wherein the porous material comprises a membrane, a gelatin or a hydrogel.

18. The method of claim 16, wherein the bead is a controlled pore bead.

* * * * *